United States Patent
Bertram

(10) Patent No.: US 8,726,904 B2
(45) Date of Patent: May 20, 2014

(54) LARYNX TUBE AND METHOD FOR THE PRODUCTION THEREOF

(75) Inventor: Volker Bertram, Sulz a.N. (DE)

(73) Assignee: VBM Medizintechnik GmbH, Sulz a.N. (DE)

( * ) Notice: Subject to any disclaimer, the term of this patent is extended or adjusted under 35 U.S.C. 154(b) by 261 days.

(21) Appl. No.: 13/418,389

(22) Filed: Mar. 13, 2012

(65) Prior Publication Data

US 2012/0234328 A1 Sep. 20, 2012

(30) Foreign Application Priority Data

Mar. 16, 2011 (DE) .......................... 10 2011 001 325

(51) Int. Cl.
*A61M 11/00* (2006.01)

(52) U.S. Cl.
USPC ................................ 128/207.15; 128/207.14

(58) Field of Classification Search
CPC ............ A61M 16/04; A61M 16/0434; A61M 2016/0409; A61B 17/24
USPC ........ 128/207.14, 207.15, 200.26; 604/96.01, 604/101.01, 102.02
See application file for complete search history.

(56) References Cited

U.S. PATENT DOCUMENTS

| 4,231,365 A | | 11/1980 | Scarberry | |
|---|---|---|---|---|
| 4,246,897 A | * | 1/1981 | Muto | 128/207.15 |
| 5,067,497 A | | 11/1991 | Greear | |
| 5,832,920 A | * | 11/1998 | Field | 128/207.14 |
| 7,201,168 B2 | * | 4/2007 | McGrail et al. | 128/207.14 |
| 8,434,486 B2 | * | 5/2013 | Wood et al. | 128/207.14 |
| 2001/0054425 A1 | * | 12/2001 | Bertram | 128/207.15 |
| 2005/0229933 A1 | * | 10/2005 | McGrail et al. | 128/207.14 |
| 2007/0215162 A1 | * | 9/2007 | Glassenberg et al. | 128/207.15 |
| 2008/0011304 A1 | * | 1/2008 | Stewart | 128/207.15 |

FOREIGN PATENT DOCUMENTS

WO   WO 2011/106754   9/2011

* cited by examiner

*Primary Examiner* — Steven Douglas
(74) *Attorney, Agent, or Firm* — Paul Vincent

(57) ABSTRACT

A larynx tube (10) for ventilation has a tube shaft (12), which has a ventilation lumen (18), having an oesophageal cuff (28) which is arranged on the tube shaft (12) for blocking the esophagus (14) and having a drainage channel (46) which has a drainage opening (48') which is arranged distally in respect of the oesophageal cuff (28). The drainage channel (46) is formed by a drainage pipe (44) which is arranged in a longitudinal groove (42) of the tube shaft (12) which is provided on an outer side (40) of the tube shaft (12). The drainage pipe (44) is adhesively bonded and/or welded to the tube shaft (12). The tube shaft (12) has a proximal and a distal longitudinal shaft portion (56, 58) which are adhesively bonded and/or welded to each other. The distal longitudinal shaft portion (58) is constructed as an injection-molded component.

14 Claims, 6 Drawing Sheets

LARYNX TUBE AND METHOD FOR THE PRODUCTION THEREOF

This application claims Paris Convention priority of DE 10 2011 001 325.3 filed Mar. 16, 2011 the complete disclosure of which is hereby incorporated by reference.

BACKGROUND OF THE INVENTION

The invention relates to a larynx tube and a method for the production thereof.

Acting as supraglottal respiratory tracts, larynx tubes have become established in recent years as indispensable means for temporarily protecting the airway and are used both for spontaneous respiration and positive pressure ventilation.

Larynx tubes which are commercially available have a tube shaft having a ventilation lumen. There is arranged on the tube shaft an inflatable oesophageal cuff, that is to say, an inflatable blocking collar for blocking the oesophagus, and a pharyngeal cuff for blocking the pharynx. A ventilation opening of the ventilation lumen is arranged between the two cuffs.

In order to protect the airway, the larynx tube is introduced from the mouth into the pharynx until a ventilation opening of the tube shaft comes to rest upstream of the entrance to the larynx of the person to be ventilated. The two cuffs are subsequently inflated so that sealing of the oesophagus is provided by the distal oesophageal cuff and sealing of the mouth/pharyngeal space is provided by the proximally arranged pharyngeal cuff.

In order to relieve the stomach, that is to say, to drain the stomach contents, the larynx tubes occasionally have an additional drainage channel which is constructed in the tube shaft and which has a drainage opening which is arranged distally in respect of the oesophageal cuff. Such a drainage channel allows drainage of the stomach contents and pressure relief of the stomach. It is thereby possible to counteract both any risk of aspiration and danger of injury (rupture) of the oesophagus associated with vomiting.

However, with commercially available larynx tubes, the drainage channel narrows the ventilation lumen in such a manner that medical instruments or auxiliary means, such as bronchoscopes, can pass the ventilation lumen only with difficulty or not at all.

An object of the invention is to provide a larynx tube, whose ventilation lumen is narrowed to a lesser extent by the drainage channel, whilst retaining the functionality of the larynx tube, so that medical instruments and auxiliary means, such as, for example, a bronchoscope or a suction catheter, can pass the ventilation lumen in a simplified manner. An object of the invention is further to set out a method for producing such a larynx tube.

SUMMARY OF THE INVENTION

The object relating to the larynx tube is achieved by a larynx tube having the features set out in the independent device claim and the object relating to the method by a method having the features set out in the independent method claim.

In the larynx tube according to the invention, the ventilation lumen is no longer narrowed by the drainage channel. It is thereby possible to push medical instruments, such as, for example, a bronchoscope or a suction catheter or so-called tube changers, in a simplified manner along the ventilation lumen and optionally introduce them into the trachea of a person. In particular, an endotracheal tube can also be positioned blind or with fibreoptic control (for example, by means of a bronchoscope) via the ventilation lumen of the larynx tube in the trachea of a person in order to thus achieve definitive protection of the airway. The larynx tube does not have to be removed for this, so that sufficient oxygen supply can be ensured for the person at all times. Owing to the fact that the drainage tube is arranged in a longitudinal groove of the tube shaft, the larynx tube with a (still) compact overall construction can be inserted into the pharynx (gullet) of a person in a simple manner involving little trauma. With regard to opening the jaws of a person required for the introduction of the larynx tube, the drainage tube may in particular be arranged at a lateral wall region of the tube shaft. Owing to the arrangement of the drainage channel in the longitudinal groove, it is further possible to produce a connection of the drainage tube to the tube shaft that is particularly robust and resistant to bending and shearing forces to which the larynx tube is subjected in practice. The ventilation lumen of the tube shaft may advantageously have a circular opening cross-section so that bronchoscopes and endotracheal tubes which are used in practice can be pushed through the ventilation lumen in a simplified manner.

The drainage pipe is adhesively bonded and/or welded to the tube shaft. The adhesive-bonding or weld locations may be arranged only locally or also over the entire surface in the region of mutual abutment faces of the drainage tube and the tube shaft. The ventilation lumen has a ventilation opening which is arranged laterally on the tube shaft. A ramp-like inner wall portion of the ventilation lumen is associated with the ventilation opening. It is thereby possible to remove medical instruments, such as, for example, a bronchoscope explained above, or a tube changer, a suction pipe or an endotracheal tube, in a simplified and blind manner, that is to say, without any visual verification, from the ventilation opening of the ventilation lumen, without any occurrence of undesirable positional changes of the larynx tube (dislocation). In addition, the instruments can be guided with a defined angle of emergence with respect to the larynx tube in the direction towards the entrance to the larynx of a person, which considerably facilitates its introduction into the trachea.

The tube shaft has a proximal and a distal longitudinal shaft portion which are adhesively bonded and/or welded to each other. It is thereby possible in particular to provide the distal longitudinal shaft portion with a shape which allows non-traumatic introduction and placement of the larynx tube from the mouth. The distal longitudinal shaft portion may in particular have a shape which is rounded and/or conically tapering (in a distal direction). The distal longitudinal shaft portion may also advantageously have an end portion which can be bent in a flexible manner with respect to the longitudinal axis thereof so that the larynx tube can be guided in a particularly protective manner along or around anatomical structures.

The distal longitudinal shaft portion is constructed as an injection-moulded component. The proximal longitudinal shaft portion may also be constructed as an injection-moulded component.

From a functional viewpoint, and in order to achieve the most compact structure of the larynx tube possible, the drainage channel preferably has an inner cross-section which is smaller than the ventilation lumen. The drainage tube may also have a smaller wall thickness compared with the wall thickness of the tube shaft. The inner opening cross-section of the drainage channel is advantageously sized in such a manner that a discharge tube having an outer diameter which is adapted to the anatomical size relationships of a person who is supplied with or is intended to be supplied with the larynx tube can be pushed through the drainage channel (and optionally as far as a location in the stomach of the person). Such discharge tubes are commercially available in standard sizes (outer diameter/length) for newborns, babies, children, youths and adults.

The exit of the above-mentioned medical instruments can be further simplified by the ventilation opening being constructed in a longitudinally oval manner relative to the tube shaft. In addition, it is advantageous in this regard for the ventilation opening to have an opening cross-section which corresponds to the inner cross-section of the ventilation lumen.

According to a preferred embodiment of the invention, the proximal and the distal longitudinal shaft portion are inserted one inside the other. In the region of the end portions which thus overlap, there is thus an increased contact surface-area of the two components, which can be used, for example, for an adhesively bonded or welded connection of the two longitudinal shaft portions. It is thereby also possible to provide mutual rotation prevention for the two longitudinal shaft portions in a simple manner.

The tube shaft is preferably provided with an integrated bite guard. When used in accordance with provisions, the larynx tube can thereby effectively be protected at any time against damage or misplacement of the ventilation lumen caused by biting the larynx tube. In contrast to the separate bite guard articles which are commercially available and which must be arranged only after the larynx tube has been positioned between teeth or jawbones of the person provided with the larynx tube, significantly simplified, more rapid and safer handling of the larynx tube is thereby achieved. This is particularly advantageous in the field of emergency treatment. Incorrect positioning or even loss of the bite guard is also impossible.

The bite guard may in particular have at least one wall reinforcement element which is formed on the tube shaft or embedded in the tube shaft, that is to say, the wall thereof. In the most simple case, the wall reinforcement element may extend partially or even completely around the ventilation lumen of the tube shaft.

A lighter and on the whole more compact construction of the larynx tube can be produced by there being provided two wall reinforcement elements which are formed on the tube shaft, that is to say, constructed in an integral manner therewith. The wall reinforcement elements are preferably arranged on two peripheral portions of the tube shaft which are spaced apart from each other and in particular have biting surfaces which are directed away from each other. The tube shaft can thereby be protected in a sufficiently reliable manner from being bitten on or bitten through by lower jaw teeth and upper jaw teeth and from being excessively squeezed by toothless jaw bones. Overall, it is thereby possible to counteract undesirable displacement or narrowing of the ventilation lumen.

The wall reinforcement elements may in particular be arranged in terms of cross-section in a mirror-symmetrical manner with respect to an axis of symmetry which intersects with a centre (longitudinal) axis of the ventilation lumen and a longitudinal groove axis of the longitudinal groove.

In a particularly preferred manner, the wall reinforcement elements at least partially form groove flanks of the longitudinal groove of the tube shaft. The wall reinforcement elements are thereby pulled forward from the tube shaft laterally in the direction towards the drainage channel so far that the drainage pipe can also be protected against the consequences of possibly being bitten on or bitten through.

With regard to particularly comfortable and safe handling of the larynx tube, the oesophageal cuff and a pharyngeal cuff which is arranged on the tube shaft can be inflated by means of a common ventilation line (cuff line). Alternatively, independent ventilation lines may also be associated with the two cuffs, respectively. The ventilation line(s) is/are preferably arranged at least partially in a wall of the drainage pipe and/or in a longitudinal groove of the tube shaft which is arranged, for example, at the outer side of the tube shaft.

The invention is explained in greater detail below with reference to an embodiment which is illustrated in the drawings.

The embodiment illustrated and described is not intended to be understood to be a definitive listing but is instead of exemplary character in order to describe the invention.

The Figures of the drawings illustrate the subject-matter according to the invention in a highly schematic manner and are not intended to be understood to be to scale. The individual components of the subject-matter according to the invention are illustrated in such a manner that their structure can be clearly shown.

DESCRIPTION OF THE PREFERRED EMBODIMENT

Figure 1:
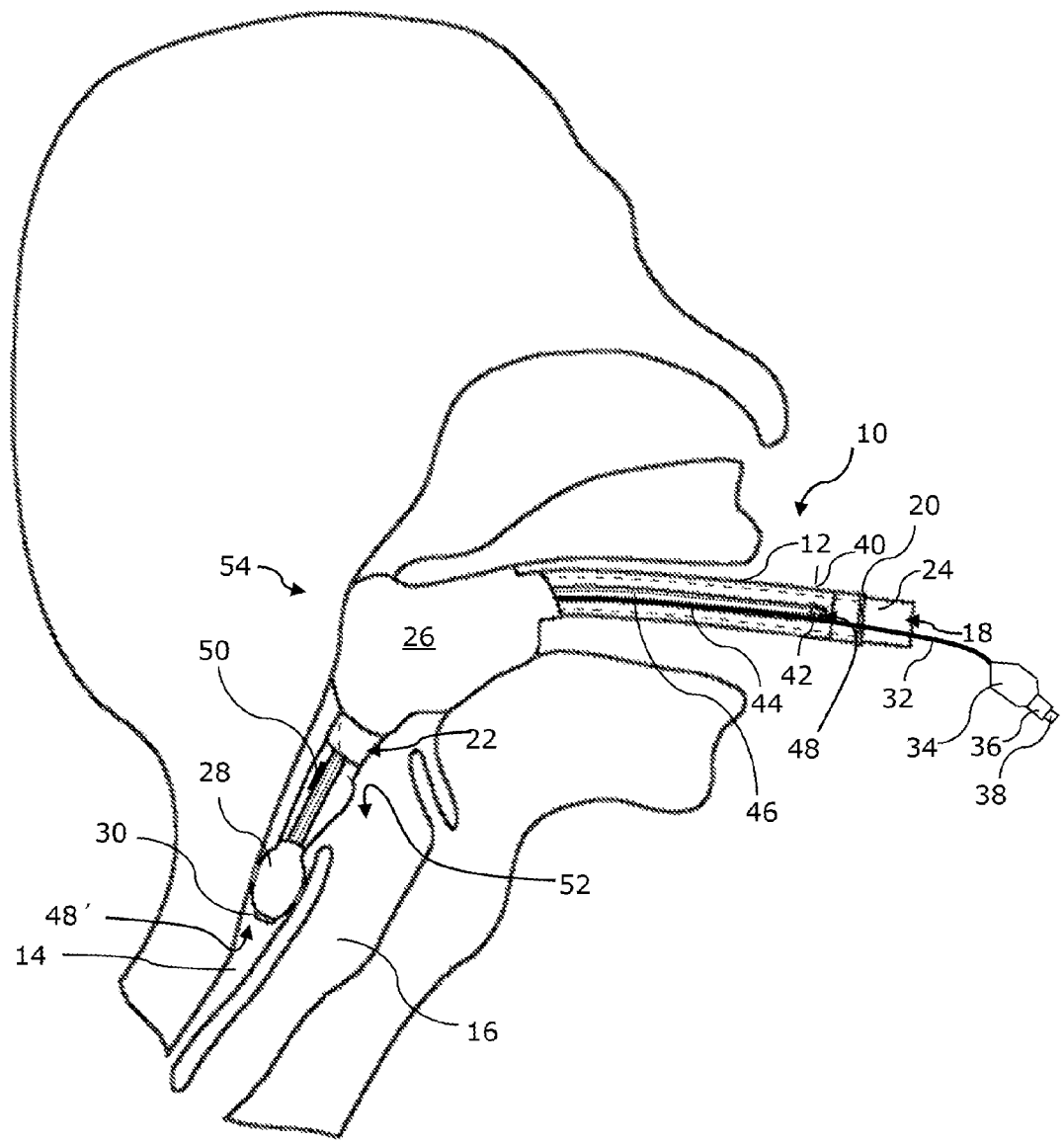
FIG. 1 is a side view of a larynx tube according to the invention with a tube shaft which has on its outer wall a longitudinal groove in which a drainage pipe is arranged.

FIG. 1 is a side view of a larynx tube 10 according to the invention. The larynx tube 10 comprises a tube shaft 12 which has an angled longitudinal profile. The angled longitudinal profile ensures that the larynx tube 10 can be inserted into the oesophagus 14 of a person in a simple and non-traumatic manner and it is not incorrectly inserted into the trachea (windpipe) 16.

The tube shaft 12 has a single ventilation lumen 18 which is illustrated in the Figures with broken lines. The ventilation lumen 18 extends from the proximal end 20 of the tube shaft 12 as far as a lateral ventilation opening 22 which is arranged in the wall of the tube shaft 12.

At the proximal end 20 of the tube shaft 12 there is arranged a connection piece 24 for the connection of a ventilation bag which is not illustrated in greater detail in the drawings, or a ventilation device.

In a manner known per se, the tube shaft 12 has two inflatable cuffs 26, 28, that is to say, block collars which engage round the tube shaft 12 in each case. A pharyngeal cuff 26 is arranged between the ventilation opening 22 and the proximal end 20 of the tube shaft 12. A distal oesophageal cuff 28 is arranged between the ventilation opening 22 and the tube shaft tip 30. The two cuffs 26, 28 may each be produced from silicone, PVC, latex or another suitable material and be constructed as so-called low-pressure cuffs in order to prevent damage to the mucous membrane.

A single ventilation line 32 is used for controlled (synchronous) inflation or deflation of the two cuffs 26, 28. The ventilation line 32 has a control ball 34 for manual verification of a cuff pressure of the two cuffs 26, 28 and a valve 36 having a connection adapter 38 for the connection of a medical syringe or a cuff pressure measuring device.

The tube shaft 12 has at its outer side 40 a longitudinal groove 42 which extends from the proximal end 22 of the tube shaft 12 as far as the tube shaft tip 30. There is arranged in the longitudinal groove 42 a drainage pipe 44 having a drainage channel 46 which is illustrated in the Figures with a dotted line. The drainage channel 46 has a proximal drainage opening 48 and a distal drainage opening 48' which is arranged, when viewed from the ventilation opening 22, downstream of the oesophageal cuff 28, that is to say, distally in respect of the oesophageal cuff 28 of the tube shaft 12. The drainage channel 44 has, in the embodiment illustrated in this instance, a circular (clear) inner diameter (I.D.) of 5 millimeters. The drainage pipe 44 is adhesively bonded to the tube shaft 12 in the region of the mutual abutment faces and, in the embodiment illustrated in this instance, made from PVC. However, the drainage pipe 44 may also be produced from a different material. An X-ray-resistant marking 50 is arranged in an axial direction of the tube shaft 12 so as to be directly distal in respect of the ventilation opening 22 on the drainage pipe 44 so that the respective position of the larynx tube 10 can be readily examined by means of X-ray diagnosis. The X-ray-resistant marking 50 may alternatively also extend over the entire length of the drainage pipe 44.

The two cuffs 26, 28 extend completely around the drainage pipe 44 and the tube shaft 12.

The ventilation opening 22 of the tube shaft 12 is arranged in this instance in accordance with provisions at the height of the entrance to the larynx 52 and is directed towards it. The oesophageal cuff 28 is inflated and abuts the oesophagus 14 in a sealing manner. The pharyngeal cuff 26 is also inflated and abuts the pharynx 54 in a sealing manner. The ventilation lumen 18 of the tube shaft 12 is consequently connected to the trachea 16 via the ventilation opening 22 and is sealed (in a downward direction) by the oesophageal cuff 28 with respect to the oesophagus 14 (and stomach) and in an upward direction by the pharyngeal cuff 26 with respect to the mouth/pharyngeal space.

Figure 2A:
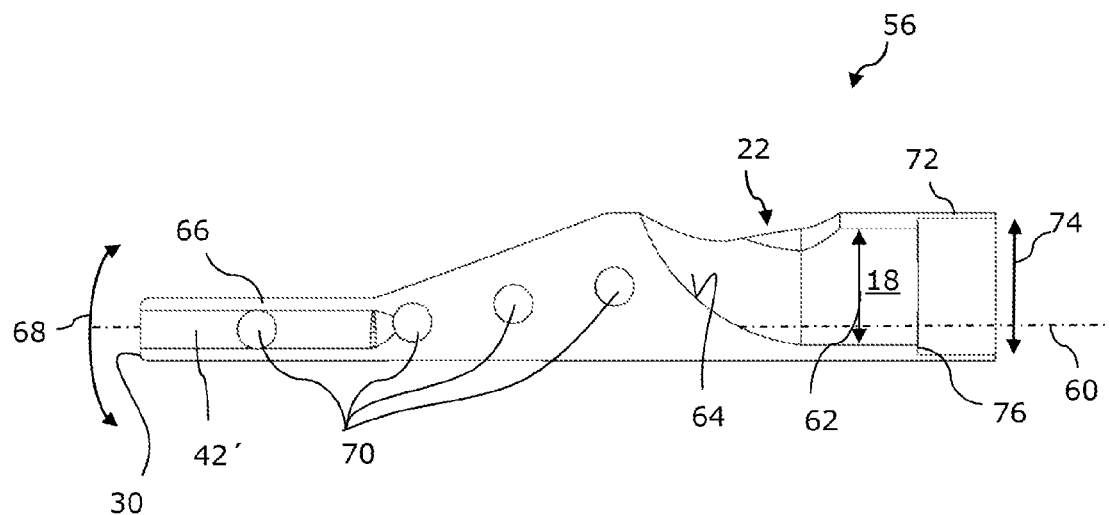
FIG. 2 is a longitudinal section (FIG. 2a) and a perspective view (FIG. 2b) of a distal longitudinal shaft portion of the larynx tube according to claim 1, respectively.
Figure 2B:
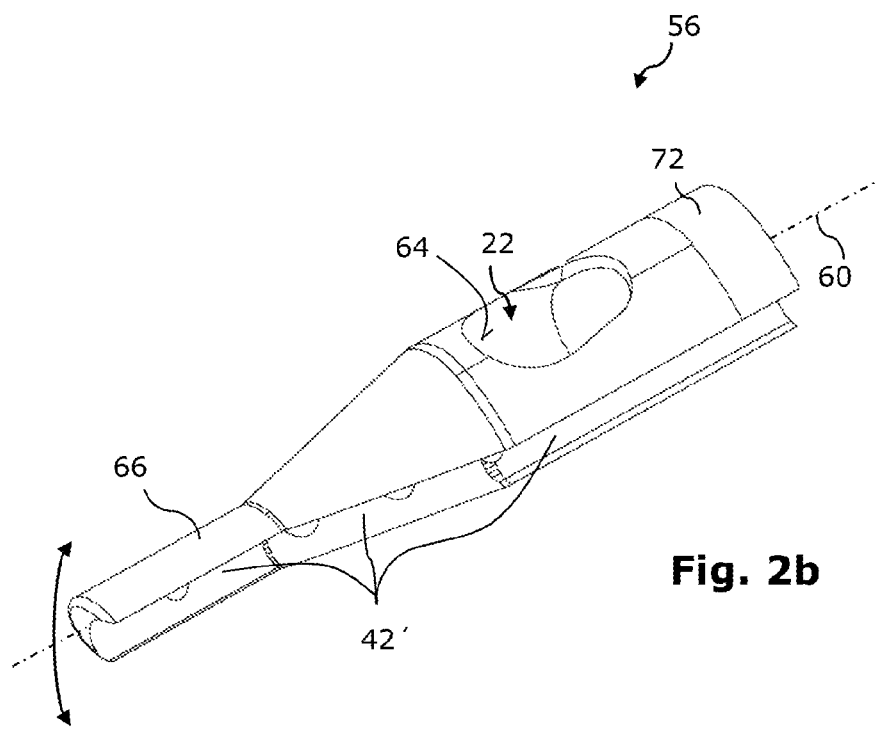
Figure 3A:
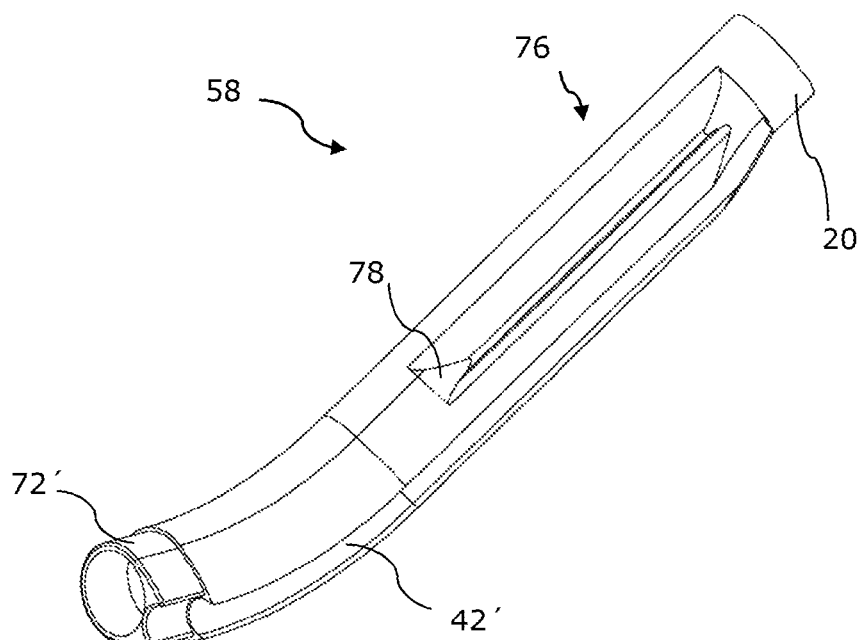
FIG. 3 is a perspective view (FIG. 3a) and an end-face view (FIG. 3b) of a proximal longitudinal shaft portion of the larynx tube according to FIG. 1, respectively.
Figure 3B:
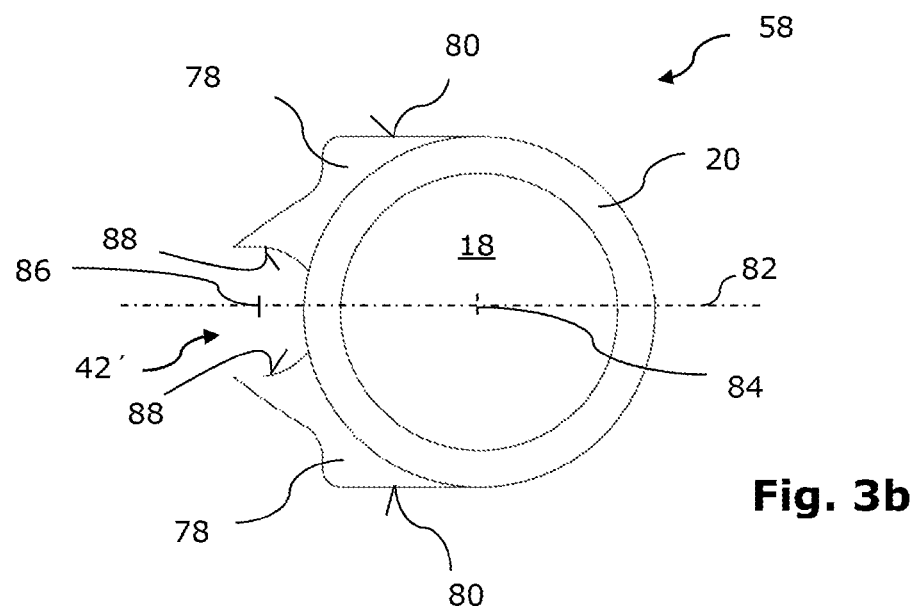

As can be seen in greater detail from FIGS. 2 and 3, the tube shaft 12 comprises two axially joined longitudinal shaft portions, a distal longitudinal shaft portion 56 illustrated in FIGS. 2a and 2b and a proximal longitudinal shaft portion 58 illustrated in FIGS. 3a and 3b. The two longitudinal shaft portions 56, 58 are reproduced without the cuffs and the drainage pipe for the purposes of illustration.

The distal longitudinal shaft portion 56 has the ventilation opening 22 of the ventilation lumen 18 of the tube shaft. The ventilation opening 22 is constructed in a longitudinally oval manner with respect to a longitudinal axis 60 of the distal longitudinal shaft portion 56 and has a cross-section which corresponds to the inner diameter 62 of the ventilation lumen 18. A ramp-like inner wall portion 64 of the ventilation lumen 22 is associated with the ventilation opening 22, through which medical instruments can be guided at a defined angle with respect to the ventilation lumen 18 from the ventilation opening 22.

The distal longitudinal shaft portion has a shape which is generally rounded and which tapers conically in the direction towards a tongue-like pointed extension 66, by means of which the larynx tube 10 can be positioned in a particularly non-traumatic manner. The tongue-like pointed extension 66 can be resiliently bent with respect to the longitudinal axis 60 of the distal longitudinal shaft portion 56 in the direction of the arrow 68. Blind hole-like recesses 70 serve to provide improved flexible deformability of the distal longitudinal shaft portion 56 which is constructed as an injection-moulded component.

The distal and the proximal longitudinal shaft portion 56, 58 each have longitudinal groove portions 42' of the longitudinal groove 42 of the tube shaft 12 (FIG. 1).

A collar-like coupling portion 72 which is associated with the proximal longitudinal shaft portion 58 (FIG. 2b) has a cross-section 74 which is widened with respect to the inner diameter 62 of the ventilation lumen 18 and an annular abutment face 76 for the proximal longitudinal shaft portion 58.

As illustrated in FIG. 3a, the proximal longitudinal shaft portion 58 is provided with a coupling portion 72' which can be inserted in an accurately fitting manner into the collar-like coupling portion 72 of the distal longitudinal shaft portion and can be adhesively bonded or welded thereto.

A bite guard 76 serves to protect the proximal longitudinal shaft portion 58 and has, in the embodiment illustrated in this instance, two strip-like wall reinforcement elements 78 which are formed on the proximal longitudinal shaft portion 56. In FIG. 3a, for the purposes of illustration, only one of the two wall reinforcement elements 78 is illustrated.

As can be seen in greater detail from FIG. 3b, the two wall reinforcement elements 78 have planar biting surfaces 80 which face away from each other in order to prevent potential damage to teeth when biting on the larynx tube 10. The strip-like wall reinforcement elements 78 are arranged in a mirror-symmetrical manner relative to an axis of symmetry 82 which intersects with a centre axis 84 of the ventilation lumen 18 and a longitudinal groove axis 86. The wall reinforcement elements 78 form groove flanks 88 of the longitudinal groove 42.

Figure 4:
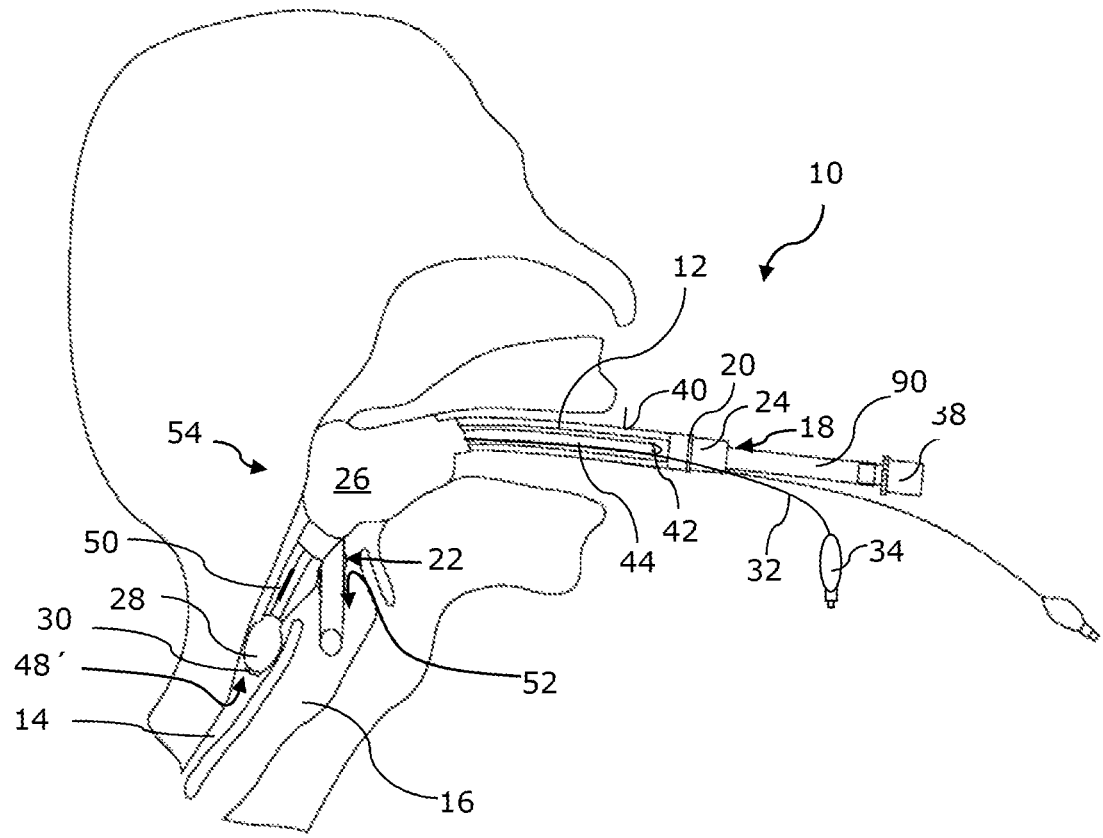
FIG. 4 is a side view of the larynx tube according to FIG. 1, through which an endotracheal tube is guided.

FIG. 4 illustrates the larynx tube 10 at a time when an endotracheal tube 90 which is constructed in known manner is being introduced into the trachea 16 via the ventilation lumen 18 thereof.

The endotracheal tube 90 is guided by the ramp-like inner wall portion 64 (FIG. 2a) out of the larynx tube 10 at an optimum angle for the tracheal intubation, that is to say, the insertion of the endotracheal tube into the trachea 16. After pushing the endotracheal tube 90 further forwards into the trachea 16 as far as a desired position, the larynx tube 10 is pulled out over the endotracheal tube 90 which is intended to be secured in its desired (tracheal) position towards the mouth and removed. Further ventilation is subsequently carried out via the endotracheal tube 90.

Figure 5A:
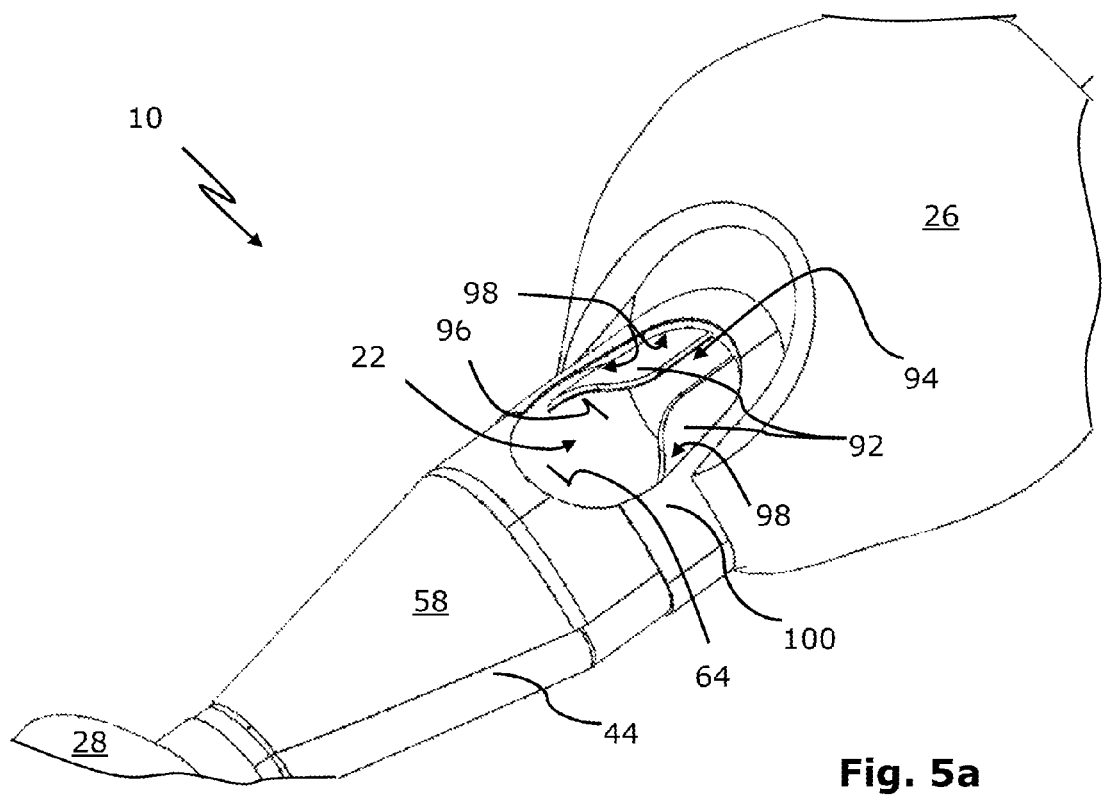
FIG. 5 is a perspective view (FIG. 5a) and a cross-section (FIG. 5b) of an alternative embodiment of the larynx tube according to the invention.
Figure 5B:
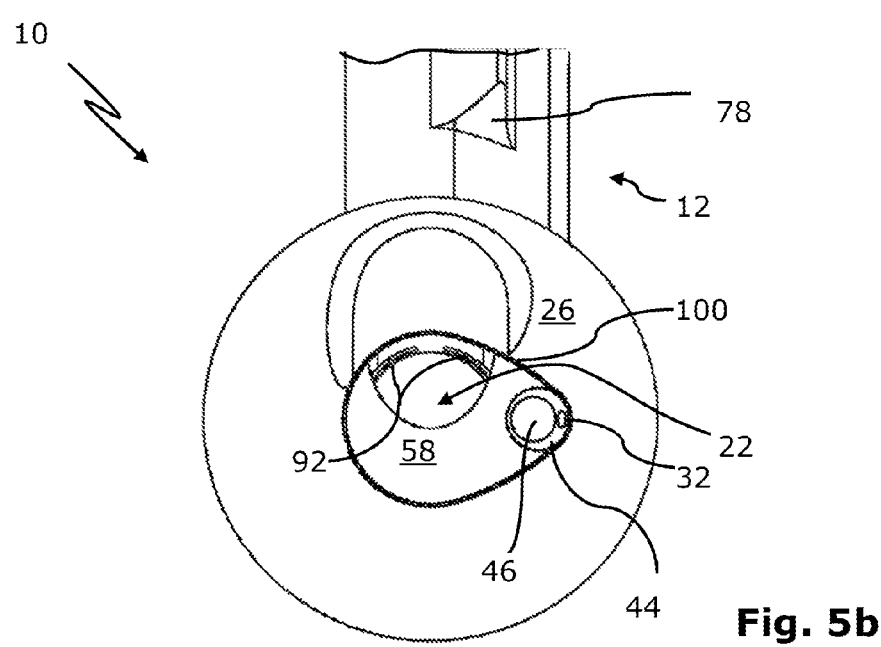

FIG. 5 shows another preferred embodiment of the larynx tube 10. The ventilation opening 22 of the distal longitudinal shaft portion 58 is provided with two elastically deformable flaps 92 to block an unwanted entry of an epiglottis of a patient (not shown) into the ventilation lumen 18. The flaps 92 are spaced from one another by a gap 94. The gap is basically arranged in the midline of the ventilation opening and extends in a longitudinal direction of the ventilation opening 22 (as well as the distal longitudinal shaft portion 58). The flaps 92 are seamlessly moulded on inner walls 96 of the ventilation lumen 18 (FIG. 2a) with their lateral and proximal edges 98. The flaps 92 are thus arranged in a recessed fashion with respect to an outside surface 100 of the distal longitudinal shaft portion 58 thereby allowing for an easy and atraumatic placement of the larynx tube 10 in a patient. When an instrument, as for example, an bronchoscope or an endotracheal tube, is advanced out of the ventilation lumen 18, both flaps 92 are elastically spread apart and lifted upwardly in direction of the ventilation opening 22 by the instrument thereby facilitating a passage of the instrument. The flaps 92 are designed such as to elastically move back to their position as shown in FIG. 5 after removal of the instrument.

Figure 6:
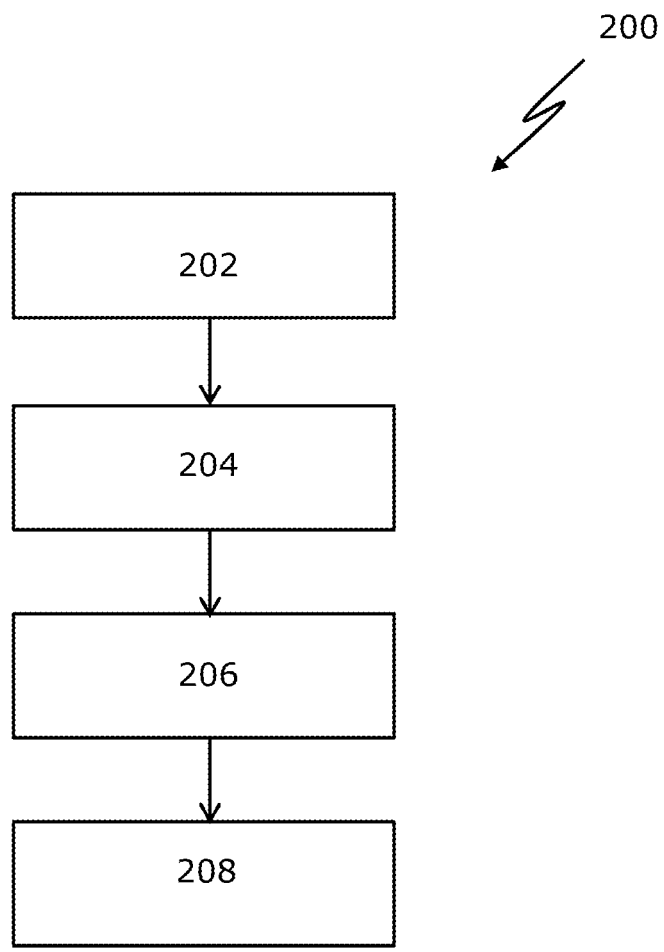
FIG. 6 is a diagrammatic view of method steps for producing a larynx tube according to the invention.

The production 200 of the larynx tube is explained briefly below with additional reference to FIG. 6.

In a first step 202, the two longitudinal shaft portions 56, 58 of the tube shaft 12 are produced by means of an injection-moulding operation. The proximal longitudinal shaft portion can also be extruded. The longitudinal shaft portions 56, 58 provided are subsequently inserted one inside the other with the coupling portions 72, 72' and adhesively bonded and/or welded 204 to each other thereby.

In another step 206, the drainage pipe 44 is placed in the longitudinal groove 42 of the tube shaft 12 and adhesively bonded and/or welded to the tube shaft.

In another step 208, the two cuffs 26, 28 are fitted with their common ventilation pipe 32 to the tube shaft 12 and the drainage pipe 44.

I claim:

1. A larynx tube for ventilation purposes, the tube comprising:
    a tube shaft having a ventilation lumen and a longitudinal groove formed in an outer side of said tube shaft, said tube shaft having a proximal and a distal longitudinal shaft portion which are adhesively bonded and/or welded to each other, said distal longitudinal shaft portion being constructed as an injection-molded component, wherein said ventilation lumen has a ventilation opening which is disposed laterally in said distal longitudinal shaft portion of said tube shaft, said distal longitudinal shaft portion having a conically tapering shape;
    an esophageal cuff which is disposed on said tube shaft for blocking an esophagus; and
    a drainage pipe forming a drainage channel having a drainage opening disposed distally with respect to said esophageal cuff, said drainage pipe disposed in said longitudinal groove of said tube shaft and adhesively bonded and/or welded to said tube shaft.

2. The larynx tube of claim 1, wherein said ventilation opening has a ramp-like inner wall portion.

3. The larynx tube of claim 1, wherein said drainage channel has a smaller inner cross-section than said ventilation lumen.

4. The larynx tube of claim 1, wherein said ventilation lumen has a ventilation opening which is arranged laterally on said tube shaft and with which a ramp-like inner wall portion of said ventilation lumen is associated.

5. The larynx tube of claim 1, wherein said proximal and said distal longitudinal shaft portion are inserted one inside an other.

6. The larynx tube of claim 1, wherein said tube shaft is provided with a bite guard.

7. The larynx tube of claim 6, wherein said bite guard has at least one wall reinforcement element which is formed on said tube shaft or embedded in said tube shaft.

8. The larynx tube of claim 7, further comprising two wall reinforcement elements which are formed on said tube shaft and which have biting surfaces.

9. The larynx tube of claim 8, wherein said biting surfaces face away from one an other.

10. The larynx tube of claim 8, wherein said wall reinforcement elements are arranged, in terms of cross-section, in a mirror-symmetrical manner with respect to an axis of symmetry which intersects with a center axis of said ventilation lumen and a longitudinal groove axis of said longitudinal groove.

11. The larynx tube of claim 8, wherein said wall reinforcement elements at least partially form groove flanks of said longitudinal groove of said tube shaft.

12. The larynx tube of claim 1, further comprising a pharyngeal cuff disposed on said tube shaft, wherein said esophageal cuff and said pharyngeal cuff are structured for inflation by a common ventilation line which is at least partially arranged in a wall of said drainage pipe and/or in said longitudinal groove of said tube shaft.

13. The larynx tube of claim 1, wherein said ventilation opening is provided with two elastically deformable flaps, said two flaps being spaced apart from each other by a gap which is disposed in a longitudinal direction of said ventilation opening.

14. A method for producing the larynx tube of claim 1, the method comprising the steps of:
    a) forming the tube shaft from a proximal and a distal longitudinal shaft portion which are adhesively bonded and/or welded to each other;
    b) arranging a drainage pipe in a longitudinal groove which is arranged at an outer side of the tube shaft; and
    c) welding and/or adhesively bonding the drainage pipe to the tube shaft.

\* \* \* \* \*